United States Patent
Sadeghpour et al.

(10) Patent No.: US 9,962,325 B2
(45) Date of Patent: *May 8, 2018

(54) COMPOSITIONS CONTAINING THEOBROMINE AND THEIR USE IN TREATING TOOTH HYPERSENSITIVITY

(71) Applicant: THEOCORP HOLDING CO., LLC, Metairie, LA (US)

(72) Inventors: Arman Sadeghpour, Metairie, LA (US); Tetsuo Nakamoto, Kenner, LA (US)

(73) Assignee: THEOCORP HOLDING CO., LLC, Metairie, LA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/408,060

(22) PCT Filed: Mar. 14, 2013

(86) PCT No.: PCT/US2013/031371
§ 371 (c)(1),
(2) Date: Dec. 15, 2014

(87) PCT Pub. No.: WO2013/191763
PCT Pub. Date: Dec. 27, 2013

(65) Prior Publication Data
US 2015/0132233 A1    May 14, 2015

Related U.S. Application Data

(60) Provisional application No. 61/662,181, filed on Jun. 20, 2012.

(51) Int. Cl.
| | |
|---|---|
| *A61K 31/522* | (2006.01) |
| *A61K 33/06* | (2006.01) |
| *A61P 1/02* | (2006.01) |
| *A61K 8/49* | (2006.01) |
| *A61K 33/14* | (2006.01) |
| *A61K 33/42* | (2006.01) |
| *A61K 6/00* | (2006.01) |
| *A61K 6/033* | (2006.01) |
| *A61K 8/19* | (2006.01) |
| *A61K 8/24* | (2006.01) |
| *A61Q 11/00* | (2006.01) |

(52) U.S. Cl.
CPC .......... *A61K 8/4953* (2013.01); *A61K 6/0017* (2013.01); *A61K 6/033* (2013.01); *A61K 8/19* (2013.01); *A61K 8/24* (2013.01); *A61K 31/522* (2013.01); *A61K 33/06* (2013.01); *A61K 33/14* (2013.01); *A61K 33/42* (2013.01); *A61Q 11/00* (2013.01)

(58) Field of Classification Search
USPC ......................................... 423/308
See application file for complete search history.

(56) References Cited

U.S. PATENT DOCUMENTS

| | | | | |
|---|---|---|---|---|
| 5,571,502 A | * | 11/1996 | Winston | A61K 8/19 424/49 |
| 5,919,426 A | * | 7/1999 | Nakamoto et al. | 423/308 |
| 6,183,711 B1 | * | 2/2001 | Nakamoto et al. | 423/308 |

FOREIGN PATENT DOCUMENTS

| | | | | |
|---|---|---|---|---|
| JP | 2008-247870 | * | 10/2008 | ........... A61K 31/353 |
| WO | 2011100671 A2 | | 8/2011 | |

OTHER PUBLICATIONS

Janet Roloff, "Chocolate Constituent Bests Fluoride." Science News: Magazine of the Society for Science & the Public; May 22, 2007 (p. 1-3).*
De Oliveira, LD et al., "Effects of Coffea arabica on *Streptococcus mutans* adherence to dental enamel and dentine", Braz J Oral Sci. 2007;6(23): pp. 1438-1441.
Jenkins, GN, "Enamel Protective Factors in Food", J Dent Res. 1970;49(6): pp. 1318-1325.
Kargul, B et al., "Effect of Theobromine on Enamel Surface Hardness: An in-vitro Study", In: The Preliminary Program for IADR General Session, 2010.
Veeresha, KL et al. "Cheese Coffee and Caries" J Orofacial & Health Sci. 2012;3(1): pp. 14-18.
International Search Report from corresponding PCT/US2013/031371, dated Jun. 28, 2013.

* cited by examiner

*Primary Examiner* — Walter E Webb
(74) *Attorney, Agent, or Firm* — McBee Moore Woodward & Vanik IP, LLC; Susan McBee; Chester Moore

(57) ABSTRACT

Compositions and methods for reducing oral sensitivity, increasing the systemic health of a mammal, occluding a dentinal tubule within a mammalian tooth, and/or depositing a precipitate on the surface of a mammalian tooth are provided, said compositions comprising theobromine (3,7-dimethylxanthine, the principal alkaloid in *Theobroma cacao*).

13 Claims, 11 Drawing Sheets

COMPOSITIONS CONTAINING THEOBROMINE AND THEIR USE IN TREATING TOOTH HYPERSENSITIVITY

CROSS-REFERENCE TO RELATED APPLICATIONS

This application is a § 371 National Stage Application of PCT/US2013/031371, filed Mar. 14, 2013, which claims the benefit of U.S. Provisional Application No. 61/662,181, filed Jun. 20, 2012.

BACKGROUND

1. Field of the Invention

The present disclosure relates to dental sensitivity treatment compositions that contain theobromine (3,7-dimethylxanthine, the principal alkaloid in *Theobroma cacao*) and the uses thereof. Uses include the treatment of dentine sensitivity or hypersensitivity, and effective occlusion of dental tubules.

2. Description of Related Art

Dental decay is the most widespread and prevalent disease plaguing humankind. Erosion of tooth enamel is the primary cause of painful dentine hypersensitivity. Gum recession is also a contributing factor to exposed dentin. Erosion of the enamel can occur from the acidic foods such as citrus fruits or wine that can significantly damage the outer enamel and cause the exposure of open dentinal tubules. Hypersensitive teeth are also sensitive to cold, heat, air, and sugar-ridden foods.

Dentin, along with enamel, cementum, and pulp, is one of the four major components of teeth. It is a calcified tissue and is usually covered by enamel (on the crown) and cementum (on the root), and completely surrounds the pulp. Dentin is, morphologically, radially striated in structure, due to the large number of microtubules (dentinal tubules) that radiate outward through the dentin from the center pulp cavity to the periphery of the dentin (the exterior cementum or enamel border). The tubules are roughly two microns (2 µm) in diameter at the base (near the pulp) and become more narrow (about 0.5 µm) at the periphery (toward the gums), and contained fluid and cellular structures (cytoplasmic extensions of odontoblasts that once formed the dentin, and maintain it; the odontoblast cell bodies are aligned along the inner aspect of dentine against a layer of predentine, where they also form the peripheral boundary of the dental pulp). Due to the dentinal tubules, dentin has some permeability, which can elevate the sensation of pain and the rate of tooth decay. In a healthy oral cavity, these tubules are covered by enamel and cementum (which is in turn covered by the gingival tissue/gums).

In the United States, alone, dental hypersensitivity affects roughly 40 million adults, among which roughly 25% are chronically affected (Kanakpka J A, *Dent. Clin North Am.* 1990; 34(3):545-60). Most incidences of tooth hypersensitivity begin in the age range of 30-39 and worsen with age. Exposed dentinal tubules allow increased hydrodynamic flow and a direct pressure gradient that is able to excite nerve endings in the dental pulp. The hydrodynamic flow can be increased by various environmental factors including, but not limited to, cold, heat, air pressure, dryness, sugar, sour or acidic stimuli, or mechanical forces (e.g., toothbrushing) acting on the tooth. In addition, brushing with abrasive toothpaste may abrade the dentin surface and open dentinal tubules if combined with corrosive agents. Excitation of exposed nerve endings in the dentinal pulp can be incredibly painful, and is the root cause of dentinal hypersensitivity.

Compositions known in the art use potassium nitrates, bioactive glass compositions, strontium chloride, strontium acetate, or amorphous calcium phosphates as treatments, yet doubts regarding their effectiveness remain. Allegedly, these compounds promote the deposition of minerals within the lumen of dentinal tubules and on the exposed dentin, thereby preventing transmission of noxious stimuli. According to at least one review, however, there is no strong evidence to support the efficacy of potassium salts for dental hypersensitivity. Poulsen S, et al. Potassium nitrate toothpaste for dentine hypersensitivity. Orchardson R, Gillam D G. The efficacy of potassium salts as agents for treating dentin hypersensitivity. *J Orofac Pain.* 2000; 14(1):9-19. None of the compositions known in the art have used or suggested using theobromine as a catalyst for nearly instant and complete dentinal tubule occlusion.

The solution to this technical problem is provided by the embodiments characterized in the claims.

SUMMARY

The present disclosure relates to compositions and methods for treating and/or reducing dentine hypersensitivity, as well as methods and compositions for treating and/or preventing caries.

More specifically, the present disclosure relates to the use of theobromine (an additive to commercially available dental products and foods) as a natural treatment that is able to fully occlude dentinal tubules in a treatment period significantly shorter than currently available dentinal hypersensitivity treatment methods. Due to the safety profile of the compound, this makes theobromine a particularly useful additive to a variety of dental, food, and beverage related products.

Compositions according to the instant disclosure that contain theobromine for treating and/or reducing dentinal hypersensitivity include but are not limited to: toothpaste, mouthwash, dental floss, over the counter trays, coated strips, gels, orthodontic and pediatric varnishes, dental cements or adhesives, polishing/prophylaxis pastes, tooth bleaching agents, cavity filling materials and resins (both UV and non-UV reactive), and endodontic materials including gutta percha.

Foods of particular interest for the reduction of dentinal hypersensitivity include, but are not limited to: gums, mints, tooth-friendly candies, chews, breads, ready to eat cereals, oatmeal, sports and isotonic beverages, energy drinks, meal replacement beverages (non-milk and milk based), vitamin or enhanced bottled waters, tea, soy milk, gelatins, yogurts, yogurt drinks, fruit smoothies, powdered or liquid flavored drinks, and calcium chews.

In one embodiment is provided an oral care composition comprising: isolated theobromine, or a salt or double salt thereof; a source of calcium selected from the group consisting of calcium chloride calcium carbonate, calcium gluconate, calcium phosphate, calcium acetate, and combinations thereof; a source of phosphate selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof.

In one embodiment is provided a method of reducing oral sensitivity comprising applying to the surface of a mammalian tooth an oral care composition comprising: isolated theobromine, or a salt or double salt thereof; a source of calcium selected from the group consisting of calcium chloride, calcium carbonate, calcium gluconate, calcium phosphate, calcium acetate, and combinations thereof; a source of phosphate selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof.

In one embodiment is provided a method of maintaining or increasing the systemic health of a mammal comprising applying a composition to an oral surface of a mammal at least once a day for a duration of time, wherein the composition comprises: isolated theobromine, or a salt or double salt thereof, or a co-crystal comprising theobromine; a source of calcium selected from the group consisting of calcium chloride, calcium carbonate, calcium gluconate, calcium phosphate, calcium acetate, and combinations thereof; a source of phosphate selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof.

In one embodiment is provided a method of occluding a dentinal tubule within the surface of a mammalian tooth comprising applying to the tooth surface a composition comprising: isolated theobromine, or a salt or double salt thereof, or a co-crystal comprising theobromine; a source of calcium selected from the group consisting of calcium chloride, calcium carbonate, calcium gluconate, calcium phosphate, calcium acetate, and combinations thereof; a source of phosphate selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof.

In one embodiment is provided a method of depositing a precipitate on the surface of a mammalian tooth comprising applying to the tooth surface a composition comprising: isolated theobromine, or a salt or double salt thereof, or a co-crystal comprising theobromine; a source of calcium selected from the group consisting of calcium chloride, calcium carbonate, calcium gluconate, calcium phosphate, calcium acetate, and combinations thereof; a source of phosphate selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof.

The composition may have a pH of from about 3 to about 11, from about 4 to about 10, from about 5 to about 9, from about 6 to about 8.5, from about 6 to about 8, from about 6.5 to about 7.5, about 7, from about 7 to about 11, from about 8 to about 11, from about 8 to about 10, from about 8.5 to about 9.5, about 9, from about 3 to about 7, from about 3 to about 6, from about 3 to about 5, preferably from about 4 to about 5, more preferably from about 4.5 to about 4.8, and even more preferably about 4.8.

The composition may further comprise at least one isotonic agent. The isotonic agent may be a polyhydric alcohol. The polyhydric alcohol may be selected from the group consisting of xylitol, sorbitol, mannitol, maltitol, lactitol, isomalt, erythritol, arabitol, glycerol, and combinations thereof. The composition of said method may further comprise at least one thickener. The thickener may be selected from the group consisting of methyl cellulose, carboxymethyl cellulose, ethyl cellulose, hydroxypropyl cellulose, and combinations thereof. The composition may further comprise an antibacterial agent, an antimicrobial agent, or combinations thereof. The antibacterial agent may be selected from the group consisting of triclosan, hydrogen peroxide, methyl-4-hydroxybenzoate, clove oil, and combinations thereof.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION OF A PREFERRED EMBODIMENT

Figure 1:
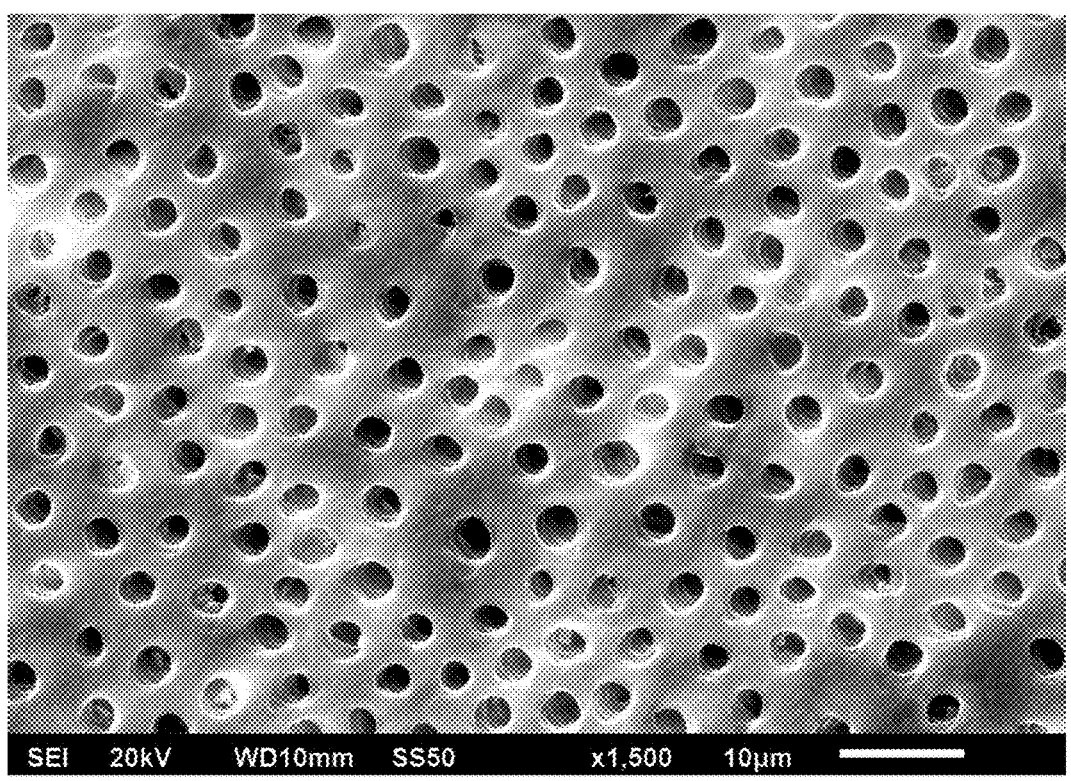
FIG. 1 shows patent dentinal tubules from a control tooth specimen.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

Current methods for assessing dental tubule occlusion rely on the preparation of dentin block samples that are treated with a composition for a period of time to measure: 1) the number of dental tubules exposed/open; 2) the number of partially occluded dental tubules; and 3) the number of completely occluded dental tubules.

Preliminary data of samples shows that the theobromine-containing formulation of the instant claims is significantly and surprisingly more effective than former proposed dentinal tubule occlusion treatments. The results presented herein show that after one directed use of the instant formulation over 95% of all dentinal tubules are partially or completely occluded (compare FIGS. 1 and 3 vs. FIGS. 2 and 4).

The theobromine-containing compositions and formulations may contain from about 0.0100 to about 0.1%, to about 1.0%, to about 2.5%, to about 5%, to about 10%, to about 20%, to about 50%, or to about 99% by weight, preferably from about 0.01% to about 0.1%, to about 1.0%, to about 2.5%, to about 5%, to about 10%, to about 20%, or to about 50% by weight, and more preferably from about 0.1% to about 0.1%, to about 1.0%, to about 2.5%, to about 5%, to about 10%, to about 20%, to about 50% of isolated theobromine, depending on the formulation.

The theobromine-containing compositions and formulations may contain conventional excipients such as binding agents (e.g., syrups such as corn syrup, acacia, gelatin, sorbitol, tragacanth, polyvinylpyrrolidone, polyethylene glycols (PEG), waxes and other fats, cocoa butter, cocoa butter substitutes, hydrogenated tallow, hydrogenated vegetable oils, hydrogenated cotton seed oil, palm kernel oil, soybean oil, stannol esters, glycerol esters, polyalcohol esters, polyoxyethylene esters of hydrophilic and hydrophobic balances from 0.5 to above 20 and polyethylene glycols, monosaccharides, oligosaccharides (dextrose, dextrose monohydrate, lactose, mannose, fructose, and derivatives and mixtures thereof), polysaccharides, gum solutions, hydrogenated starch hydrolates, glycerine, and mixtures thereof; fillers (e.g., silicon dioxide, sugars, starches, lactose, sucrose, sorbitol, fructose, talc, stearic acid, magnesium stearate, dicalcium phosphate, erythritol, xylitol, mannitol, maltitol, isomalt, dextrose, maltose, lactose, microcrystalline celluloses, maize-starch, glycine, and mixtures thereof); lubricants (e.g., magnesium stearate, calcium stearate, talc, starches, silicon dioxide, and mixtures thereof); disintegrants (e.g., starch, polyvinylpyrrolidone, sodium starch glycollate, microcrystalline cellulose, and mixtures thereof); bonding agents (e.g., polyethylene glycols in solid form, monoglycerides (40-90% glycerides of vegetable or animal fats), acetylated monoglycerides, hydro-colloidal gums, other emulsifiers or fats and mixtures thereof); or pharmaceutically acceptable wetting agents (e.g., sodium lauryl sulphate).

Theobromine-containing compositions and formulations useful for the instant methods have been disclosed in International Publication No. WO 2011/100671, which claims priority to U.S. Provisional Application No. 61/303,774, the disclosures of which are hereby incorporated by reference herein their entirety.

MATERIALS & METHODS

Selection of Root Dentin and Dentin Block Preparation

Figure 5:
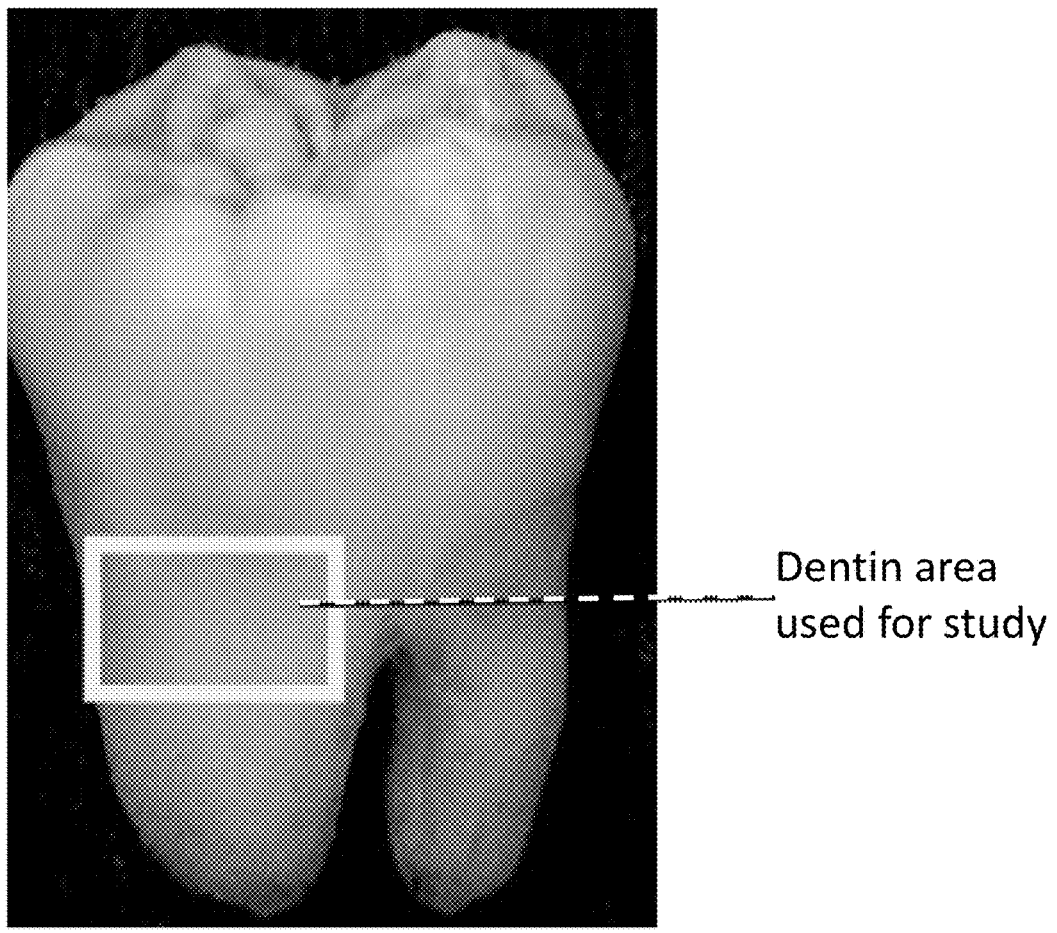
FIG. 5 shows a representative human molar, and the inset box indicates the dentin area used for dentin block preparations for the studies described herein.

Freshly extracted human molar teeth stored in 2-isopropyl-5-methylphenol (IPMP, or thymol) disinfectant were collected, cleaned of debris, and examined for smooth dentin area (see FIG. 5). A water-cooled diamond wire saw (Well Diamond Wire Saws, Inc. Norcross, Ga., USA) was used to cut dentin blocks measuring approximately 6-7 mm×1.5 mm. Blocks having a height of about 0.75 mm and a smooth working surface were obtained by polishing the samples using diamond lapping films in a MultiPrep precision polishing machine (Allied High Tech Products, Inc. CA, USA) initially with 30 µm diamond grit and finishing with 1 µm grit to obtain a smooth finish. The resulting blocks are referred to as "samples." Final sample size was 6-7 mm length×1.5 mm width×0.75 mm height. The non-working surface area was marked with an indelible pencil to distinguish it from the working surface. At least one or two vertical or horizontal dentin blocks were obtained from the root of each molar. Bifurcations and the cement-enamel junction were avoided.

Creating Control and Test Specimens

Each sample (6-7 min length×1.5 min width×0.75 mm height) was sectioned into two halves using a water-cooled diamond wire saw to produce two blocks measuring 3.5 mm length×1.5 mm width×0.75 mm height, one serving as the test sample and the other as control (that is, matching control and test samples were obtained). In other words, each test sample has a corresponding control sample. The cutting edge of both specimens was also marked with pencil.

Removal of Smear Layer

Acid etching and sonication was performed to remove smear layer and debris formed during sample preparation and to obtain patent dentin tubules. Both halves (control and test) of each samples were sonicated simultaneously (Branson Sonifier 450, Danbury, Conn., USA) for no longer than 2 minutes (power setting 1) in a 200 ml beaker containing 6% citric acid, pH 2.0 (by wt: granular/powder citric acid added to distilled water). After etching with citric acid, the specimens were sonicated for 2 minutes (power setting 2) in distilled water, pH 7.0. Following sonication, the samples were carefully dried as follows. The samples were initially dried with Kimwipes and then placed in a clean petri dish with working surfaces facing upward (away from the bottom of the petri dish). The petri dish was covered with sparsely-perforated Parafilm to avoid contamination by dust, and then air-dried overnight (no longer than 16 hours) in a laminar flow hood.

SEM Examination of Control Dentin Block

Prior to study, the control samples were examined via scanning electron microscopy (SEM) to ensure quality of specimen preparation and patent dentinal tubules. Upon establishment of uniformity and integrity of specimen surface, scanning electron micrographs of three randomly selected areas from each specimen were recorded. Samples with surface artifacts and occluded dentinal tubules were discarded. The SEM images of the selected samples were recorded and saved for future comparative analysis. Etched test dentin blocks that corresponded to control den in blocks with uniform open dentinal tubules throughout the sample were chosen for study.

Preliminary In Vitro Study

Prior to the clinical study described below, two test samples were brushed for one minute using a soft-bristled toothbrush and a theobromine-containing toothpaste composition. The toothpaste was allowed to remain on the test samples for one additional minute, after which they were rinsed with 10 mL of water for 10 seconds. The test samples were then immersed in artificial saliva, as were the two matching control samples. Subsequently, the two test and two control samples were removed from the artificial saliva containing sources of calcium and phosphate (see, for example, International Publication No. WO 2011/100671, which claims priority to U.S. Provisional Application No. 61/303,774, the disclosures of which are hereby incorporated by reference herein their entirety) and allowed to air-dry in a petri dish for 24 hours. After air-drying, the samples were sputter-coated with gold/palladium alloy. The sputter-coated samples were then visualized and analyzed via SEM (JEOL USA Inc.; Model No. JSM-6610LV). A defined area on the surface of each dentin block was examined using Scanning Electron Microscopy (SEM) at a magnification of 1500× (see FIGS. 1-4).

Clinical Study

Scanning Electron Microscope (SEM) Examination of Control Dentin Block

Prior to clinical study, the control samples were examined with SEM to ensure quality of specimen preparation and patent dentinal tubules. Upon establishment of uniformity and integrity of specimen surface, scanning electron micrographs of three randomly selected areas were recorded. Samples with surface artifacts and occluded dentinal tubules were discarded. The SEM images reading of the selected sat were recorded and saved for future analysis. The "test" blocks corresponding to the "control" dentin blocks, with fully-open dentinal tubules throughout the sample, were chosen for study.

Storage or Samples & Construction of In Situ Appliances

Prior to and following intra-oral exposure, test samples (in an it situ appliance), were stored dry in a petri dish with their working surface facing upwards (away from the bottom of the petri dish). Care was taken not to touch the working surfaces during further procedures. Insertion of the blocks into in situ appliances was performed no earlier than two days prior to clinical study. The appliances were constructed for each human subject so that dentin blocks could be attached to a healthy molar tooth. Each appliance was based on the design of brackets used in orthodontic treatment. Each appliance consisted of an orthodontic molar pad with retentive mesh backing (Dentarium, Germany), having a ring of 0.7 mm orthodontic wire welded to it so that the ring closely encircled each dentin test-block. The dentin blocks were retained within the bracket using Intermediate Restorative Material (IRM fluoride-free temporary restoration cement), exposing only one surface of the block to the oral cavity. Then, the appliances were sterilized using ethylene oxide.

Selection of Study Objects

The study was an observer-blind, randomized, parallel group, single center, controlled clinical trial. Approximately 80 generally healthy adults meeting the necessary inclusion/exclusion criteria were enrolled (20 per treatment group). Screening visits occurred 5-7 days prior to collection of baseline measurements. At the screening visit, each subject completed a medical/dental history and read and signed an informed consent document. Following consent, each subject began a washout period and was instructed to start brushing with the assigned test toothpaste and soft-bristled toothbrush twice daily, in their usual manner. The following eligibility criteria were designed to select subjects for whom protocol treatment was considered appropriate.

General Inclusion Criteria

Subjects were required to meet all of the following inclusion criteria to be eligible for enrollment into the trial:

a Male or female at least 18 years of age in good general and oral health without any known allergy to commercial dental products or cosmetics;

Evidence of a personally signed and dated informed consent document indicating the subject (or legally acceptable representative) had been informed of all pertinent aspects of the trial; and Willingness to use the assigned products according to instructions, availability for appointments, and likelihood of completing the clinical trial.

Oral Exam Inclusion Criteria

A minimum of 18 healthy teeth exposed to the oral environment. Crowned or extensively restored teeth were not included in the tooth count;

Unrestored and sound enamel on the buccal surface of both lower first permanent mandibular molars (teeth #18, 19 and 30, 31), which had been chosen as the teeth to carry the two in situ appliances;

Absence of significant oral soft tissue pathology, based on a dentist's visual examination and at the discretion of the investigator;

Absence of removable partial dentures;

Adequate oral hygiene (i.e., daily toothbrushing, and no obvious signs of oral neglect); and Absence of extensive supragingival calculus.

General Exclusion Criteria

Subjects resenting with any of the following were excluded from the trial:

History or presence of kidney disorders or kidney stones, Crohn's Disease or other malabsorption syndromes;

History of significant adverse effects following use of oral hygiene products such as toothpastes and mouthwashes;

a Physical limitations or restrictions that could preclude use of normal oral hygiene procedures (i.e. toothbrushing, mouthrinsing, etc.);

Currently taking any antibiotics or medication that could adversely affect the salivary flow rate;

Reported allergy to drugs or chemicals used in the trial;

Use of antimicrobial agents, whether prescribed or over-the-counter, within four weeks prior to screening visit;

Receiving or planning to receive dental treatment which could affect participation, such as oral prophylaxis (emergency treatment, however, was allowed);

a Requirement for premedication prior to dental treatment;

Participation in a dental clinical trial involving oral care products within the past 30 days;

Pregnant, nursing or planning to become pregnant during the course of the study (self-reported); and Other severe, acute or chronic medical or psychiatric condition or laboratory abnormality that could possibly increase the risk associated with trial participation or could possibly interfere with the interpretation of trial results and, in the judgment of the investigator, could make the subject inappropriate for entry into the trial.

If the subject reported taking medication, a history of allergy, and/or a chronic disease which, in the opinion of the investigator, would not affect the clinical parameter(s) being assessed in the study or the safety of the subject, the subject was enrolled in the study and it was noted on the Investigator's source document.

Oral Exam Exclusion Criteria

Teeth that were grossly carious, orthodontically banded, abutment teeth for fixed or removable prostheses or third molars were not be included in the study;

Periodontal surgery and orthodontic treatment within previous 3 months;

History or current evidence of significant oral soft tissue pathology based on the dental examiner's visual examination, and at the discretion of the Investigator;

Presence of severe marginal gingivitis based on a clinical examination and discretion of the Investigator; and Visual evidence of Moderate/Advanced Periodontitis (ADA Type III, IV).

Removal of Subjects from the Study

An investigator could terminate a subject from investigational treatment in the event of:

Adverse events;

a Compliance problems;

Serious eligibility or on-study violations of the protocol;

Subject's decision to withdraw;

Withdrawal of consent; and

Protocol-specific criteria.

Trial Treatments

Subjects were randomly assigned to one of four treatment groups:

Theodent-NF—Nonfluoride-containing Theodent toothpaste (Theodent® classic; Theocorp Holding Company, Metairie, La., USA);

Sensodyne—Novamin-containing antisensitivity toothpaste (Sensodyne 5000 Nupro®; DENTSPLY Professional; York, Pa., USA);

Colgate—Standard fluoride toothpaste (Colgate Regular™; Colgate Pharmaceuticals, New York, N.Y., USA); or Theodent-F—Fluoride-containing Theodent toothpaste (Theodent® with fluoride; Theocorp Holding Company, Metairie, La., USA).

The efficacy of the four toothpastes, Theodent-NF, Sensodyne, Colgate and Theodent-F, were compared at 1 days (2 product-uses), 2 days (4 product-uses), 3 days (6 product-uses) and 7 days (14 product-uses) time points. The efficacy of each product after 2, 4, 6 and 14 product-uses were also compared to determine longitudinal effect.

Clinical Procedures subjects received a soft bristled manual toothbrush and their respective toothpaste for use throughout the duration of the study. They started a washout period and were instructed to brush two times daily, morning and just before bed, in their usual manner. On each occasion, subjects brushed for one minute using at least a one-inch strip of their respective toothpaste and then wait for another one minute before rinsing with 10 ml of water for 10 seconds. The first brushing occasion occurred at the research facility and was supervised by the Study Coordinator. Subjects were asked not to take any drink for at least 30 minutes after brushing. A diary was provided to each subject to keep a record of the number of times brushed each day. All subjects were asked to maintain their normal dietary habits. The use of any other oral hygiene product, such as mouthwashes, prescription products, etc., was prohibited.

After the 7-day washout period, the in situ appliances, made out of dentin blocks originating from extracted human teeth (see "Storage of samples & construction of in situ appliances" above), were assigned and fitted to each subject at the Baseline Visit (Visit 2-Day 1). Each subject wore four dentin specimens to permit efficacy assessments after 1 day (2 product uses), 2 days (4 product uses), 6 days (12 product uses) and 7 days (14 product uses). The appliances were fitted by a qualified dentist, who was different from the Laboratory Assistant who later processed and analyzed the samples to produce the final data. The buccal surfaces of each subject's mandibular first and second permanent molar teeth chosen to carry the appliances were carefully acid etched for 30 seconds, in accordance with current principles of dental practice, washed and dried for a further 30 seconds, and then isolated using cotton rolls. The bottom of the appliance was carefully positioned to avoid causing occlusal interference and to avoid soft tissue irritation.

Subjects were instructed to brush their teeth twice daily: in the morning; and just before bed. Subjects were instructed to brush on each occasion for one minute and then wait for an additional one minute before rinsing with 10 ml of water for 10 seconds. Subjects were instructed to avoid drinking anything for at least 30 minutes after brushing. A diary was provided to each subject to keep a record of the number of times brushed each day. All subjects were asked to maintain their normal dietary habits. The use of any other oral hygiene product, such as mouthwashes, prescription products, etcetera, was prohibited.

Immediately after attachment of the appliance (on day 1) each subject made the first use of their product under the supervision of the Study Coordinator, Each subject was instructed to arrive at the clinic on the morning of day 2 prior to using the assigned toothpaste, whereupon one of the four appliances was detached and sent to the laboratory for analysis. Immediately after detachment of the appliance, the subject was allowed to use the product supervised by the Study Coordinator. This process was repeated on day 3 (for 2 days of product use), day 4 (for 3 days of product use), and day 8 (for 7 days of product use) when the remaining dentin-containing appliances were detached after 14 product uses. The detached dentin blocks were sent to the lab for analysis immediately after detachment. Any bonding agent left on the tooth surface was carefully and completely removed with composite-removing burrs.

SEM Examination of Control Dentin Block

After detachment of the test dentin blocks from their appliances, the test dentin blocks were placed in a petri dish for air drying as described above. After 24 hours drying, the blocks were sputter-coated with gold palladium, then visualized and analyzed via SEM (JEOL USA Inc.; Model: JSM-6610LV).

Assessment of Tubule Occlusion

To determine the numbers of completely-, partially- and non-occluded dentin tubules, the image of each control block was examined side-by-side with that of the treated block. The center of the surface of each dentin block was examined using SEM and the image acquired at a magnification of 1500× (FIGS. 10B & 10C). Each acquired SEM image was assessed by two calibrated blinded examiners for the extent of tubule occlusion based the numbers of fully-open, partially- and completely-occluded dentin tubules as well as the percentage of the dentin surface covered by smear layer on each of 1500× image. The examiners were calibrated against a standard set of 20 images. Agreement to the standard set was quantified by Kappa analysis. The free-margin Kappa scores were 0.81 and 0.87 (any score >0.70 was considered to be acceptable as adequate agreement). The average of the two assessments was calculated for each specimen.

Smear Layer Deposit/Precipitate Assessment

In addition to counting the numbers of completely-, partially- and non-occluded tubules, the counting technicians also examined the image of each treated block for deposition of smear layer and/or precipitates. The percentage of area covered by smear layer deposit/precipitate was estimated in each image and reported.

Safety Assessment

Safety was assessed through observation and query of each subject at each visit during the study for any new or continuing symptoms since the previous visit and through the tabulation of adverse events. No adverse incidents were reported.

Statistical Methods

Statistical analysis of the data was conducted using statistic software (PASW Statistics 18.0, IBM), with $\alpha=0.05$ set as the level of significance. The numbers of fully-open, partially and completely closed tubules in each block were counted and expressed as a percentage of the number of tubules on the corresponding control block. The mean of the percentages of fully-open, partially and completely closed tubules were calculated for the individual products. Also the mean of the percentage of the surface area covered by deposited smear layer were calculated for each product. With one-way repeated ANOVA, followed by post hoc multi-step comparisons using Tukey's HSD test, the efficacy of the four toothpastes in occluding dentin tubules were compared based on the percentage of fully-open tubules, partially-closed tubules, completely-closed tubules, and surface covered by smear layer.

Example 1

Preliminary In Vitro Data

Preliminary data from samples derived from the preliminary in vitro study demonstrates that formulations containing theobromine are unexpectedly and surprisingly more effective than previously-available dentinal tubule occlusion treatments. The results herein demonstrate that after one directed use of a formulation containing theobromine over 95% or all dentinal tubules are containing partially or completely occluded (compare FIG. 1 vs. FIG. 2, and FIG. 3 vs. FIG. 4) with a precipitate deposited on the surfaces exposed to the theobromine-containing dentifrice.

Figure 2:
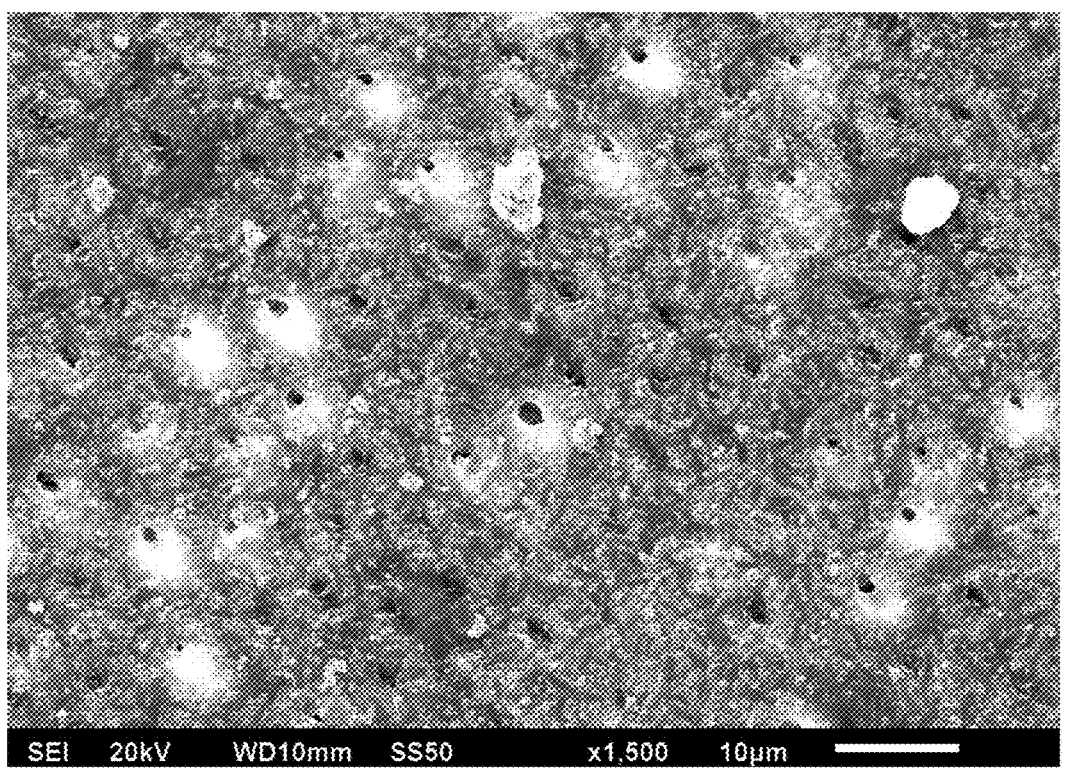
FIG. 2 shows occluded dentinal tubules from a test tooth specimen treated with a theobromine-containing dentifrice.
Figure 3:
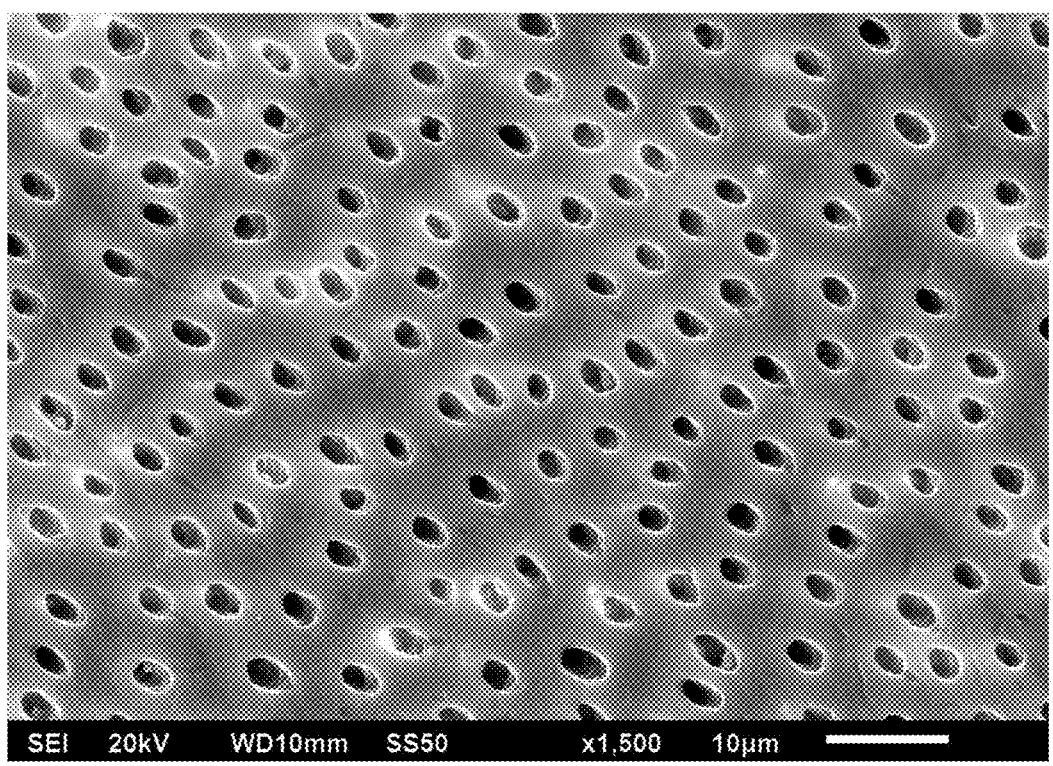
FIG. 3 shows CLINICAL TRIAL DATA: patent dentinal tubules from a control tooth specimen.
Figure 4:
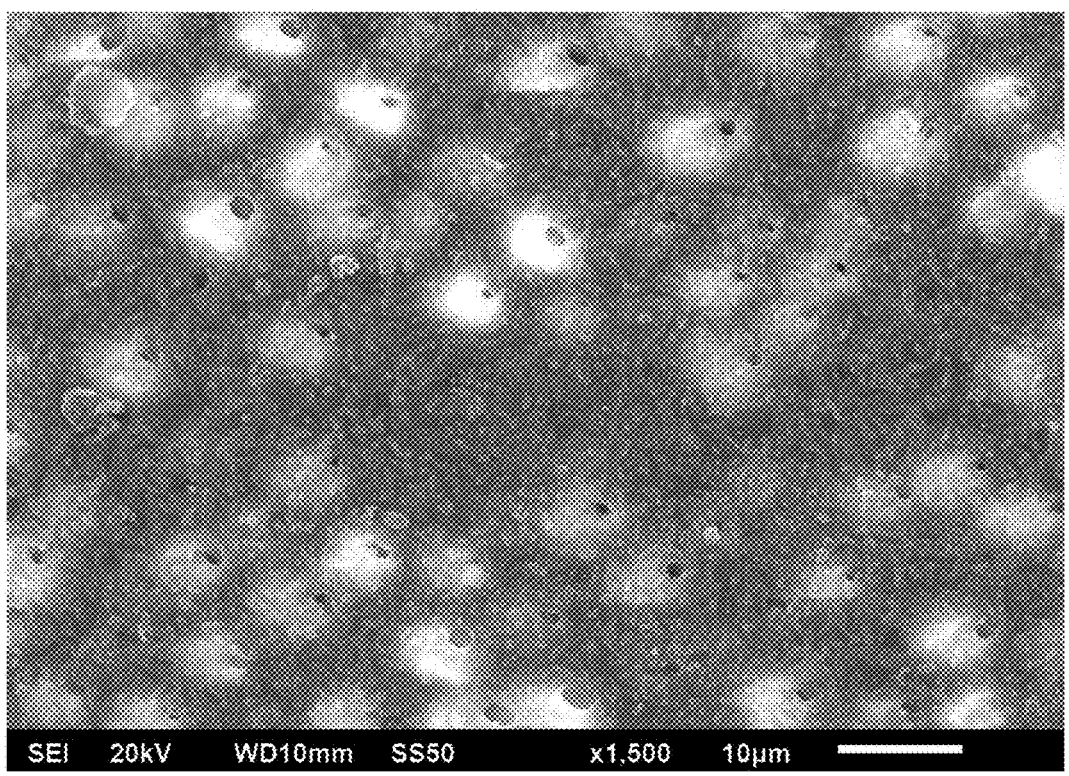
FIG. 4 shows CLINICAL TRIAL DATA: occluded dentinal tubules from a test tooth specimen treated with a theobromine-containing dentifrice.

FIGS. 1 and 3 are SEM micrographs showing control samples that were not treated with a theobromine-containing dentifrice. Patent dentinal tubules are clearly evident over the entirety of each image. FIGS. 2 and 4 are SEM micrographs showing matched test samples (derived from the same block as the control samples of FIGS. 1 and 3, respectively) that were treated with a theobromine-containing dentifrice as explained above. As shown by FIGS. 2 and 4, all dentinal tubules are either mostly or completely occluded after only one treatment with the theobromine-containing dentifrice. FIGS. 2 and 4 also show a mineral layer deposited on the tooth surfaces exposed to a theobromine-containing dentifrice.

Example 2

Results of Clinical Study

The 80 subjects recruited for clinical trial completed the study without dropout. As stated above, the efficacies of the toothpastes were compared based on four variables, i.e., the percentage of (a) completely-occluded tubules, (b) fully-open tubules, (c) partially-occluded tubules, and (d) surface area covered by smear layer.

Figure 6:
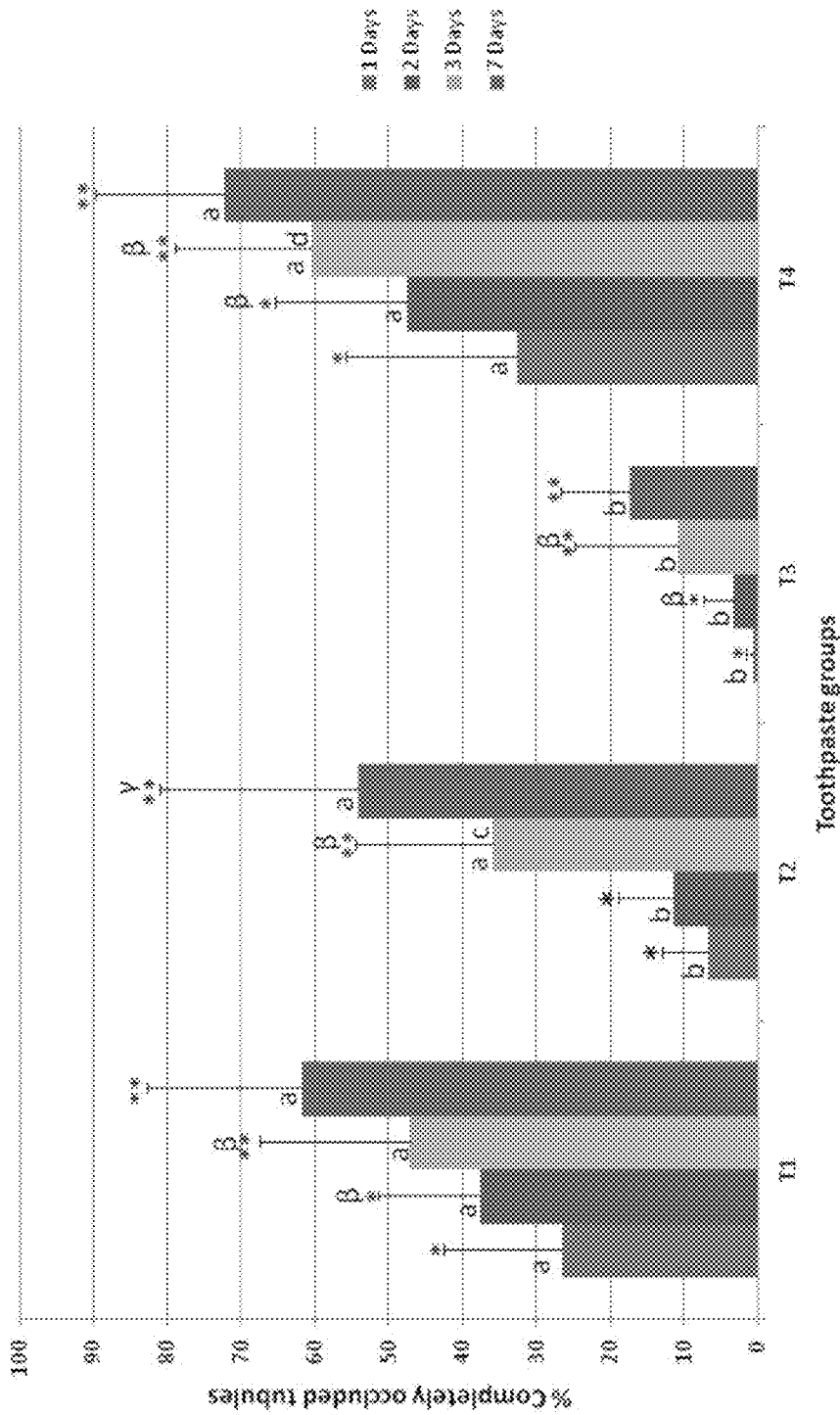
FIG. 6 shows CLINICAL TRIAL DATA: the percentage of completely occluded tubules after 1, 2, 3, and 7 days' use (2, 4, 6, and 14 uses, respectively) of the four toothpastes (T1=Theodent-NF; T2=Sensodyne; T3=Colgate; and T4=Theodent-F). For each group (T1-T4) of columns (days 1, 2, 3, & 7), "day 1" is the left-most column, followed by "day 2," then "day 3," and "day 7" as the right-most column.

FIG. 6 shows the percentage of completely occluded tubules after 1, 2, 3, and 7 days' use (2, 4, 6, and 14 uses, respectively) of the four toothpastes (T1=Theodent-NF; T2=Sensodyne; T3=Colgate; and T4=Theodent-F). Letters compared the efficacy of the four toothpastes at each usage time point (1, 2, 3 & 7 days). Different letters (i.e., a, b, c, d) denotes statistically significant difference (p<0.05) in the percentage of completely occluded tubules, while same letters denotes not significantly different. Symbols (*, **, γ, β) compared the efficacy of the same toothpaste after different lengths (1, 2, 3 & 7 days) of usage. Different symbols between columns denotes statistically significant difference (p<0.05) in the percentage of completely occluded tubules, while same symbols means not significantly different.

Figure 7:
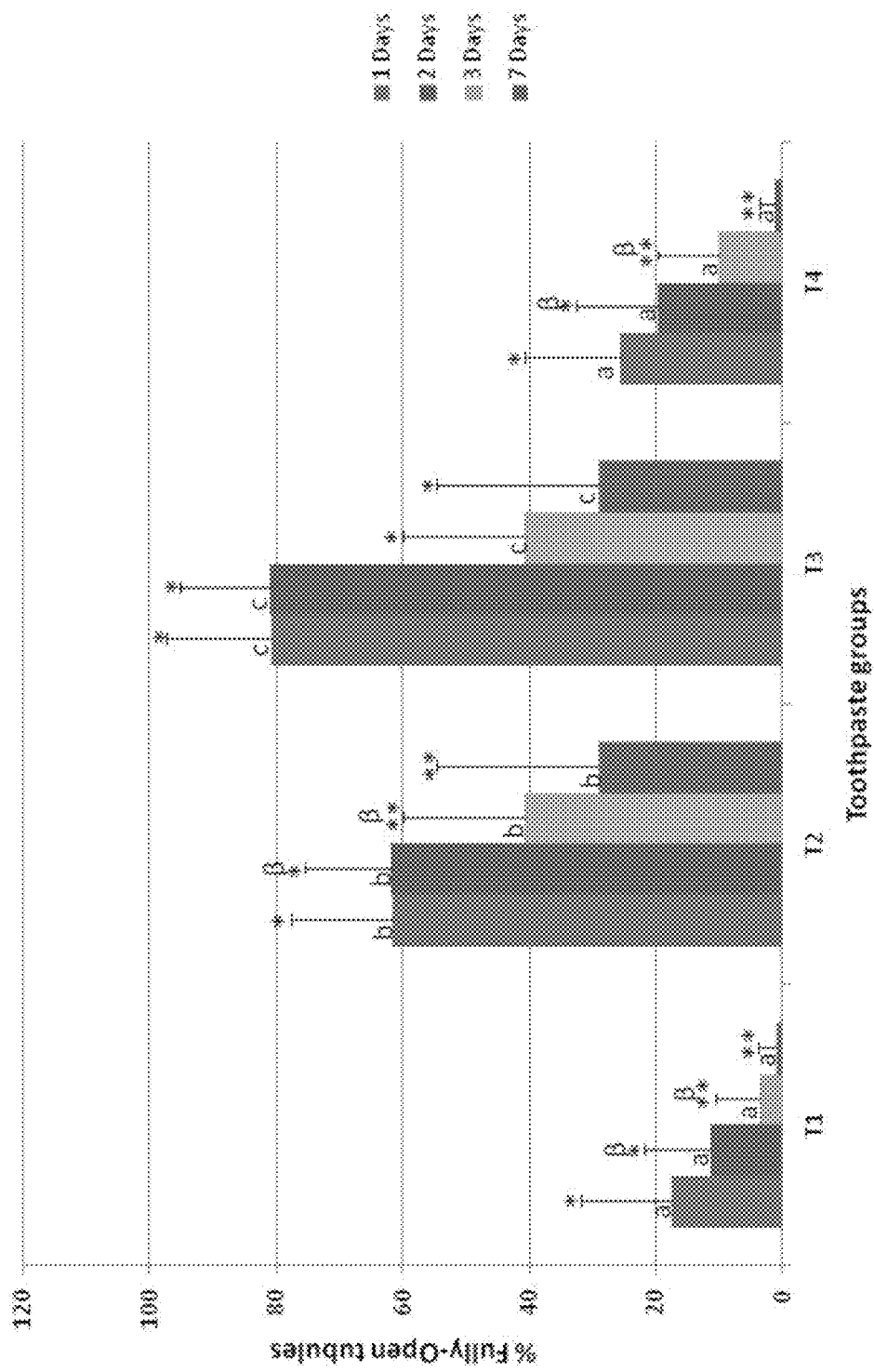
FIG. 7 shows CLINICAL TRIAL DATA: the percentage of fully-open tubules after 1, 2, 3, and 7 days' use (2, 4, 6, and 14 uses, respectively) of the four toothpastes (T1=Theodent-NF; T2=Sensodyne; T3=Colgate; and T4=Theodent-F). For each group (T1-T4) of columns (days 1, 2, 3, & 7), "day 1" is the left-most column, followed by "day 2," then "day 3," and "day 7" as the tight-most column.

FIG. 7 shows the percentage of fully-open tubules after 1, 2, 3, and 7 days' use (2, 4, 6, and 14 uses, respectively) of the our toothpastes (T1=Theodent-NF; T2=Sensodyne; T3=Colgate; and T4=Theodent-F). Letters compared the efficacy of the four toothpastes at each usage time point (1, 2, 3 & 7 days). Different letters (i.e., a, b, c) between columns denotes statistically significant difference (p<0.05) in the percentage of fully-open tubules, while same letters denotes not significantly different. Symbols compared the efficacy of the same toothpaste after different lengths (1, 2, 3 & 7 days) of usage. Different symbols between columns denotes statistically significant difference (p<0.05) in the percentage of fully-open tubules, while same symbols denotes not significantly different.

Figure 8:
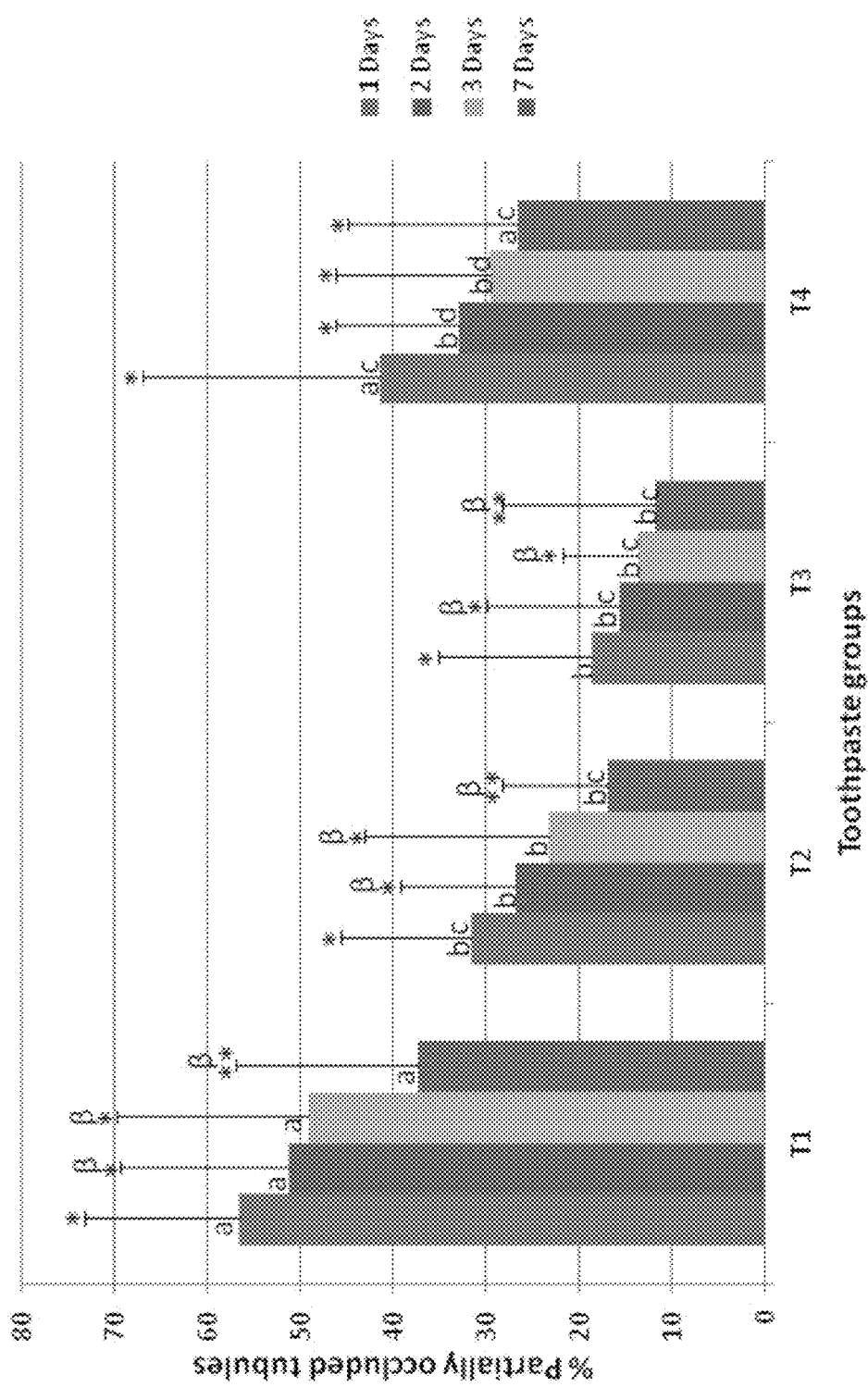
FIG. 8 shows CLINICAL TRIAL DATA: the percentage of partially-occluded tubules after 1, 2, 3, and 7 days' use (2, 4, 6, and 14 uses, respectively) of the four toothpastes (T1=Theodent-NF; T2=Sensodyne; T3=Colgate; and T4=Theodent-F). For each group (T1-T4) of columns (days 1, 2, 3, & 7), "day 1" is left-most column, followed by "day 2," then "day 3," and "day, 7" as the right-most column.

FIG. 8 shows the percentage of partially-occluded tubules after 1, 2, 3, and 7 days' use (2, 4, 6, and 14 uses, respectively) of the four toothpastes (T1=Theodent-NF; T2=Sensodyne; T3=Colgate; and T4=Theodent-F). Letters compared the efficacy of the four toothpastes at each usage time point (1, 2, 3 & 7 days). Different letters (i.e., a, b, c, d) between columns denotes statistically significant difference (p<0.05) % in partially-occluded tubules, while same letters denotes not significantly different. Symbols (*, **, β) compared the efficacy of the same toothpaste after different lengths (1, 2, 3 & 7 days) of usage. Different symbols between columns denotes statistically significantly difference (p<0.05) in partially-occluded tubules, while same symbols denotes not significantly different.

Figure 9:
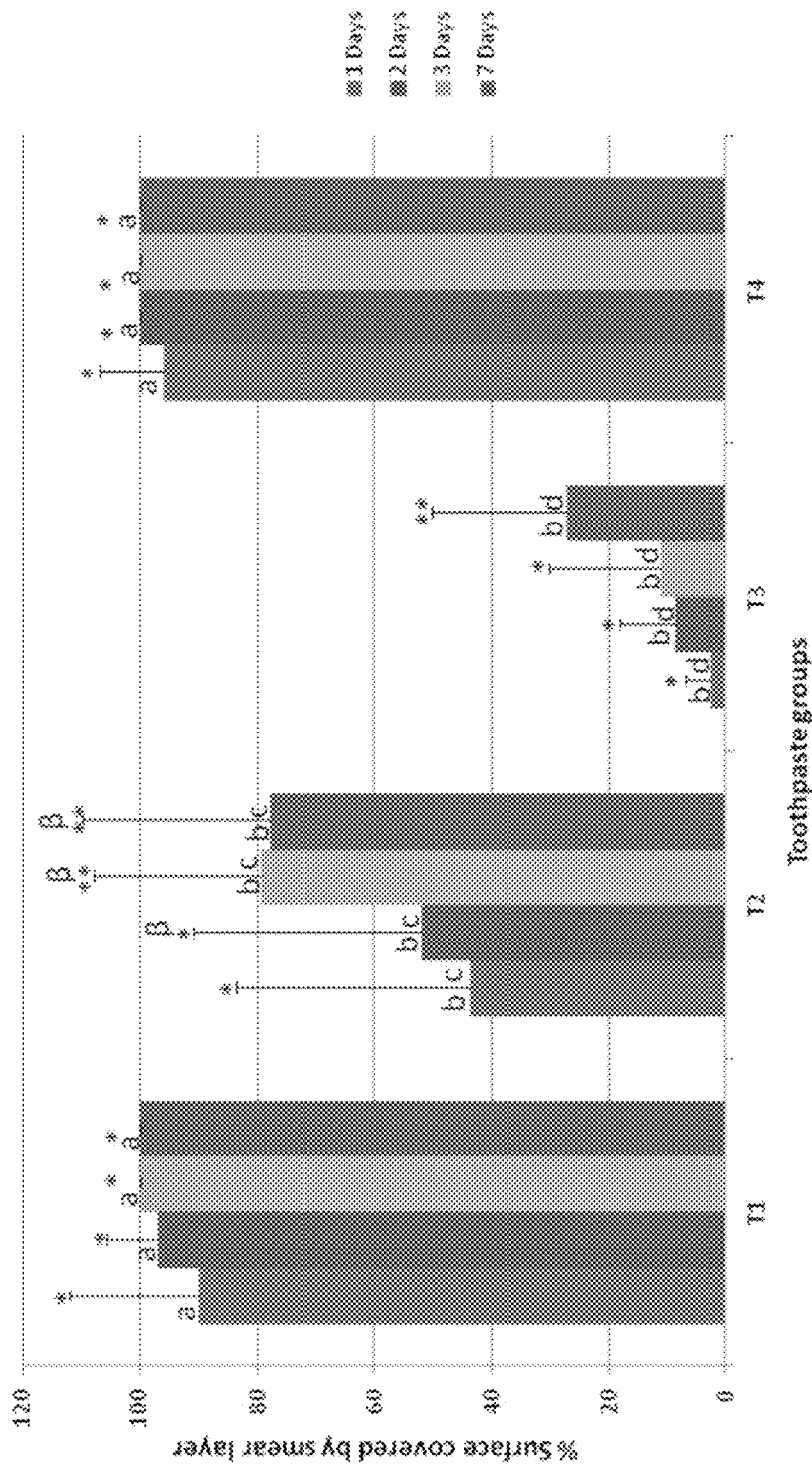
FIG. 9 shows CLINICAL TRIAL DATA: the percentage of surface area covered by deposited smear layer after 1, 2, 3, and 7 days' use (2, 4, 6, and 14 uses, respectively) of the four toothpastes (T1=Theodent-NF; T2=Sensodyne; T3=Colgate; and T4=Theodent-F). For each group (T1-T4) of columns (days 1, 2, 3, & 7), "day 1" is the left-most column, followed by "day 2," then "day 3," and "day 7" as the right-most column.

FIG. 9 shows the percentage of surface area covered by deposited smear layer after 1, 2, 3, and 7 days' use (2, 4, 6, and 14 uses, respectively) of the four toothpastes (T1=Theodent-NF; T2=Sensodyne; T3=Colgate and T4=Theodent-F). Letters compared the efficacy of the four toothpastes at each usage time point (1, 2, 3 & 7 days). Different letters a, b, c, d) between columns denotes statistically significant difference (p<0.05) % in completely occluded tubules, while same letters denotes not significantly different. Symbols (*, **, β) compared the efficacy of the same toothpaste after different lengths (1, 2, 3 & 7 days) of usage. Different symbols between columns denotes statistically significantly difference (p<0.05) % in completely occluded tubules, while same symbols denotes not significantly different.

Figure 10A:
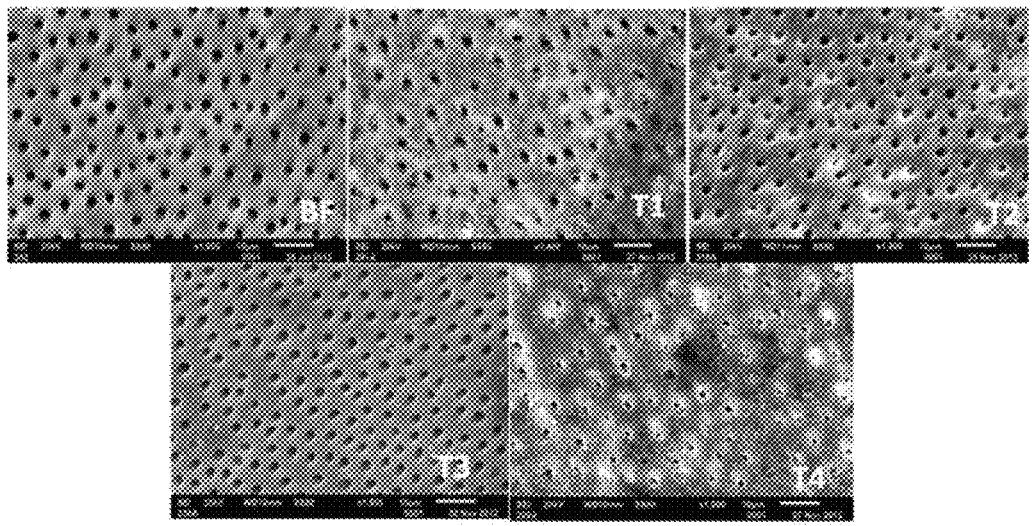
FIG. 10 shows CLINICAL TRIAL DATA: typical SEM images of the surfaces of dentin blocks with tubules before treatment (bf) and after using the four toothpastes (T1=Theodent-NF; T2=Sensodyne; T3=Colgate; and T4=Theodent-F) 2 times (1 day), 4 times (2 days), 6 times (3 days), or 14 times (7 days) at FIGS. 10A, 10B, 10C, and 10D, respectively.
Figure 10B:
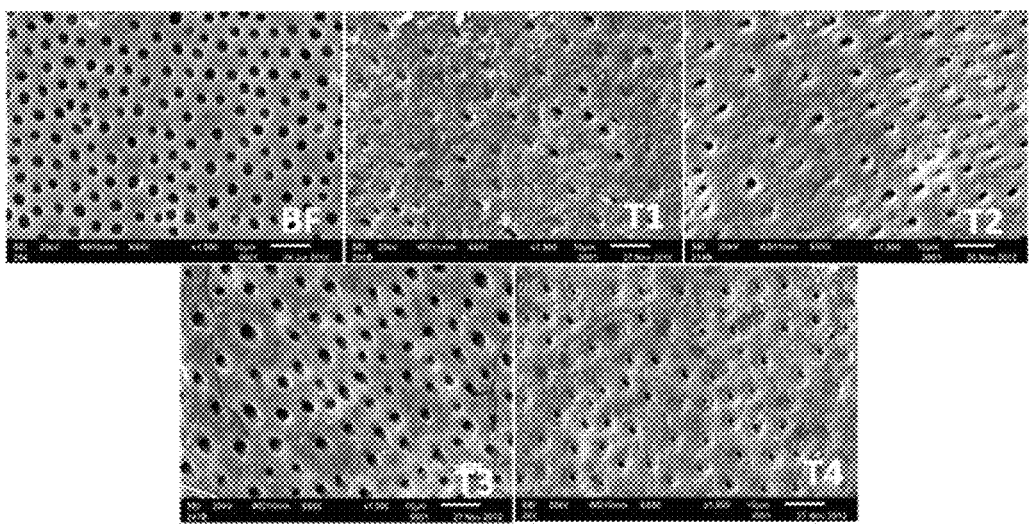
Figure 10C:
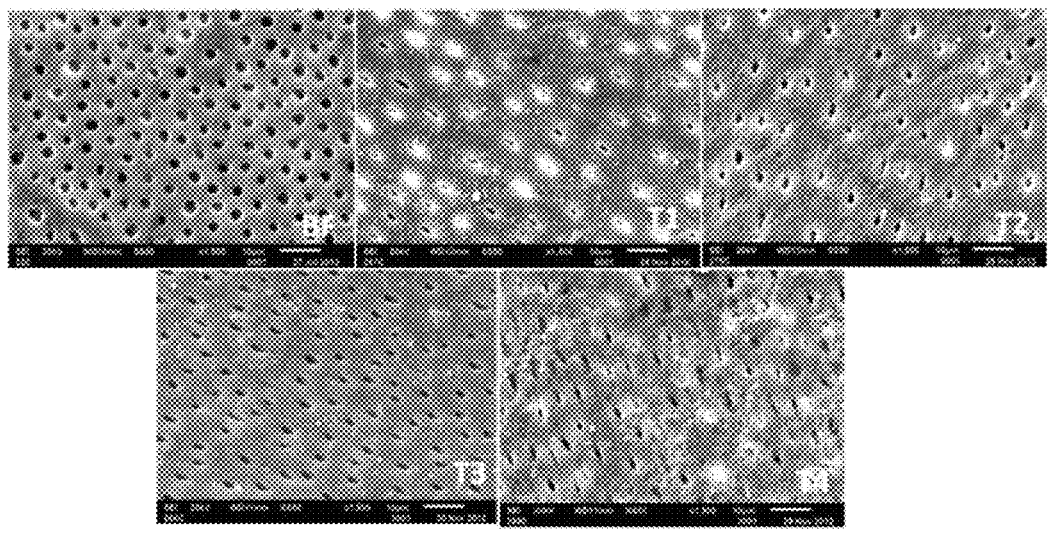
Figure 10D:
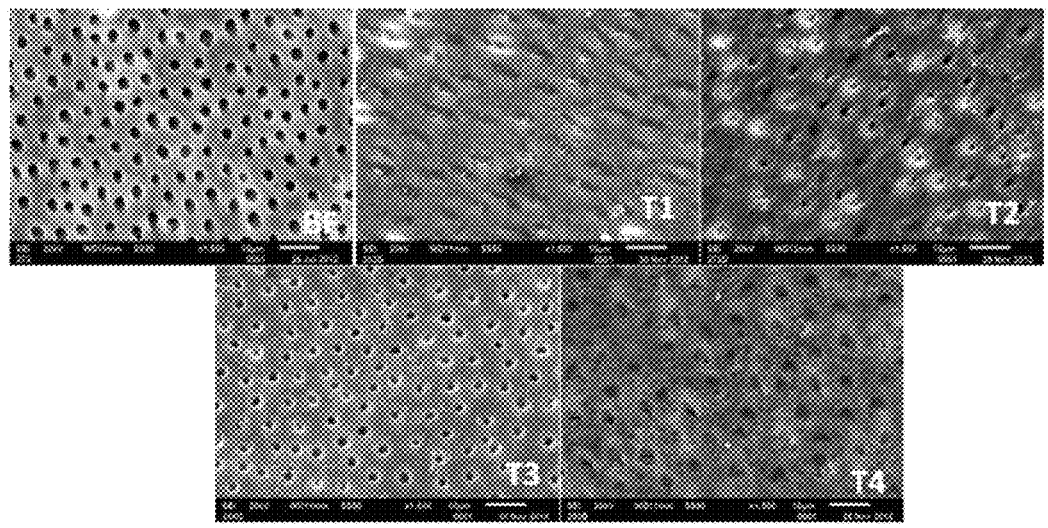

FIGS. 10A, 10B, 10C, and 10D show typical SEM images of the surface of the dentin blocks with tubules before treatment (bf) and after use of the four toothpastes (T1=Theodent-NF; T2=Sensodyne; T3=Colgate; and T4=Theodent-F). FIG. 10A shows the results obtained after 2 uses (1 day); FIG. 10B shows the results obtained after 4 uses (2 days), FIG. 10C shows the results obtained after 6 uses (3 days), and FIG. 10D shows the results obtained after 14 uses (7 days). The images demonstrate the increasing occlusion of the dentinal tubules and deposition of smear layers with increased usage of the toothpastes Theodent-NF, Sensodyne and Theodent-F but not Colgate. Colgate Regular Toothpaste deposited a negligible amount of smear layer after 14 product-uses.

The result of this clinical study demonstrated that toothpastes Theodent Classic, Theodent-with-fluoride and Sensodyne Nupro 5000® are efficacious in occluding dentin tubules as well as depositing smear layers on the dentin surface, with both Theodent Classic and Theodent-with-fluoride toothpastes being equally efficacious.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method of treating dentine hypersensitivity of at least one tooth of a mammal in need thereof, the method comprising:
   i) providing a composition comprising (a) isolated theobromine, or a salt or double salt thereof, or a co-crystal comprising theobromine; (b) a source of calcium selected from the group consisting of calcium chloride, calcium carbonate, calcium gluconate, calcium phosphate, calcium acetate, and combinations thereof; and (c) a source of phosphate selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof; and
   ii) topically applying said composition to exposed dentinal tubules of said at least one tooth of said mammal;
   wherein said composition comprises from about 1 mg/L to about 500 mg/L of theobromine, theobromine salt, or theobromine double salt, and wherein the pH of said composition is about 6.0 to about 8.5; and
   wherein said composition is selected from the group consisting of a toothpaste, a mouthwash, dental floss, a coated dental strip, a dental varnish, a dental cement, a dental adhesive, a dental polishing paste, a tooth-bleaching agent, a cavity-filling material, a dental resin, and a chewing gum.

2. The method of claim 1, wherein after two applications of said oral care composition to the exposed dentinal tubules of said tooth, at least 20% of the exposed dentin tubules of said tooth are completely occluded.

3. The method of claim 1, wherein after four applications of said oral care composition to the exposed dentinal tubules of said tooth, at least 30% of the exposed dentin tubules of said tooth are completely occluded.

4. The method of claim 1, wherein after six applications of said oral care composition to the exposed dentinal tubules of said tooth, at least 40% of the exposed dentin tubules of said tooth are completely occluded.

5. The method of claim 1, wherein after fourteen applications of said oral care composition to the exposed dentinal tubules of said tooth, at least 60% of the exposed dentin tubules of said tooth are completely occluded.

6. The method of claim 1, wherein after two applications of said oral care composition to the exposed dentinal tubules of said tooth, less than 20% of the exposed dentin tubules of said tooth are fully open.

7. The method of claim 1, wherein after four applications of said oral care composition to the exposed dentinal tubules of said tooth, less than 20% of the exposed dentin tubules of said tooth are fully open.

8. The method of claim 1, wherein after six applications of said oral care composition to the exposed dentinal tubules of said tooth, less than 10% of the exposed dentin tubules of said tooth are fully open.

9. The method of claim 1, wherein after fourteen applications of said oral care composition to the exposed dentinal tubules of said tooth, less than 5% of the exposed dentin tubules of said tooth are fully open.

10. The method of claim 1, wherein after two applications of said oral care composition to the exposed dentinal tubules of said tooth, at least 80% of the exposed dentin of said tooth is covered by deposited smear layer.

11. The method of claim 1, wherein after four applications of said oral care composition to the exposed dentinal tubules of said tooth, at least 90% of the exposed dentin of said tooth is covered by deposited smear layer.

12. The method of claim 1, wherein after six applications of said oral care composition to the exposed dentinal tubules of said tooth, at least 95% of the exposed dentin of said tooth is covered by deposited smear layer.

13. The method of claim 1, wherein after fourteen applications of said oral care composition to the exposed dentinal tubules of said tooth, at least 95% of the exposed dentin of said tooth is covered by deposited smear layer.

* * * * *